United States Patent

Chitwood

[11] Patent Number: 5,916,185
[45] Date of Patent: *Jun. 29, 1999

[54] INFLATABLE CERVICAL TRACTION OR STRETCH DEVICE

[75] Inventor: Ralph M. Chitwood, Kalispell, Mont.

[73] Assignee: Glacier Cross, Inc., Kalispell, Mont.

[ * ] Notice: This patent is subject to a terminal disclaimer.

[21] Appl. No.: 08/899,535

[22] Filed: Jul. 24, 1997

Related U.S. Application Data

[63] Continuation-in-part of application No. 08/516,007, Aug. 16, 1995, application No. 08/327,021, Oct. 21, 1994, Pat. No. 5,569,175, application No. 08/303,691, Sep. 9, 1994, Pat. No. 5,454,781, and application No. 08/120,602, Sep. 13, 1993, Pat. No. 5,441,479.

[51] Int. Cl.$^6$ ................................................. A61F 5/00
[52] U.S. Cl. ................................................ 602/18; 602/13
[58] Field of Search ................................ 602/13, 17, 18; 128/845, 869, 870, DIG. 20, DIG. 23; 5/622, 636, 637, 640, 644; 606/240, 241; 601/38

[56] References Cited

U.S. PATENT DOCUMENTS

| | | | |
|---|---|---|---|
| 2,389,690 | 11/1945 | Schreiber | 602/18 |
| 2,806,471 | 9/1957 | Breese | 602/17 |
| 3,164,151 | 1/1965 | Vere Nicoll | 602/18 |
| 3,343,532 | 9/1967 | Zumaglini | 602/18 |
| 4,099,523 | 7/1978 | Lowrey . | |
| 4,543,947 | 10/1985 | Blackstone | 602/18 |
| 4,702,235 | 10/1987 | Hong | 602/13 |
| 4,732,144 | 3/1988 | Cunanan . | |
| 4,771,493 | 9/1988 | Park . | |
| 4,805,603 | 2/1989 | Cumberland . | |
| 4,832,007 | 5/1989 | Davis, Jr. et al. . | |
| 5,060,661 | 10/1991 | Howard . | |
| 5,181,904 | 1/1993 | Cook et al. | 602/32 |
| 5,382,226 | 1/1995 | Graham . | |
| 5,403,266 | 4/1995 | Bragg et al. . | |
| 5,569,176 | 10/1996 | Graham . | |

FOREIGN PATENT DOCUMENTS

| | | |
|---|---|---|
| 3318938 | 11/1984 | Germany . |
| 3905115 | 8/1990 | Germany . |

*Primary Examiner*—Jeanne M. Clark
*Attorney, Agent, or Firm*—Thomas R. Vigil

[57] ABSTRACT

The cervical traction or stretch device comprises: an inflatable bladder or bellows having a central U-shaped space so that the bladder or bellows can extend at least part way around the neck of a user, and a pumping mechanism coupled to the bladder or bellows and operable by a user for pumping air into the bellows. The bladder or bellows has an upper side and a lower side. The lower side is constructed and arranged to be positioned adjacent a user's shoulders and exert pressure thereagainst when inflated. And the upper side is constructed and arranged to engage and exert pressure against the base of a user's head.

4 Claims, 5 Drawing Sheets

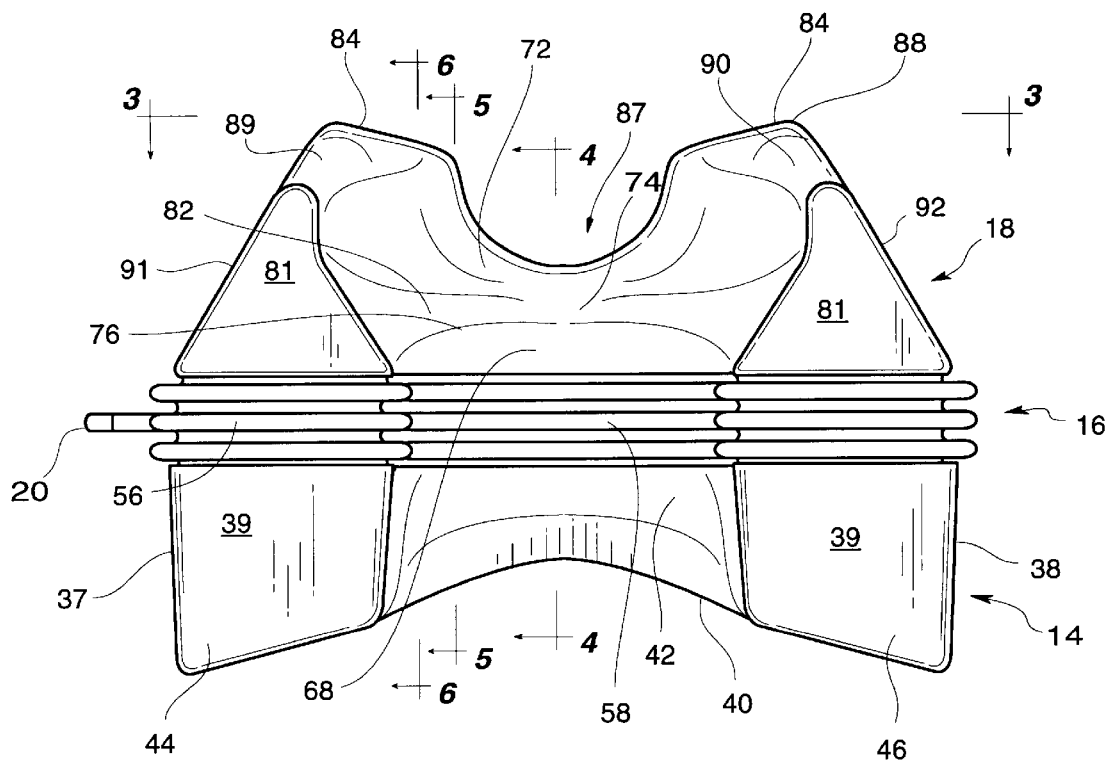
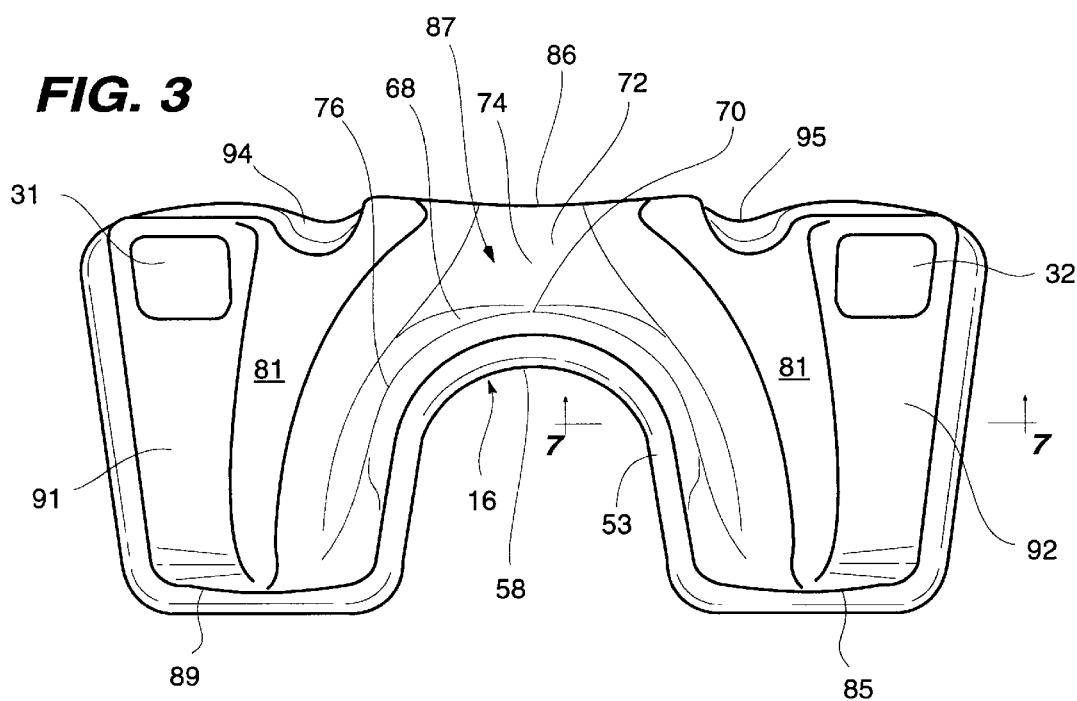

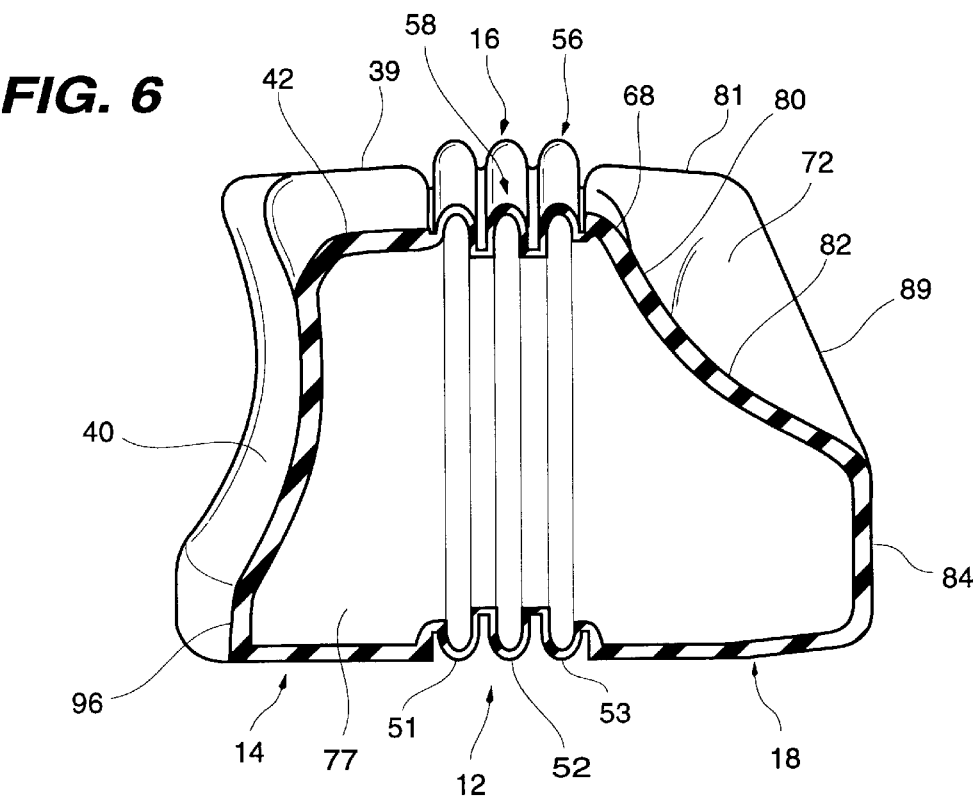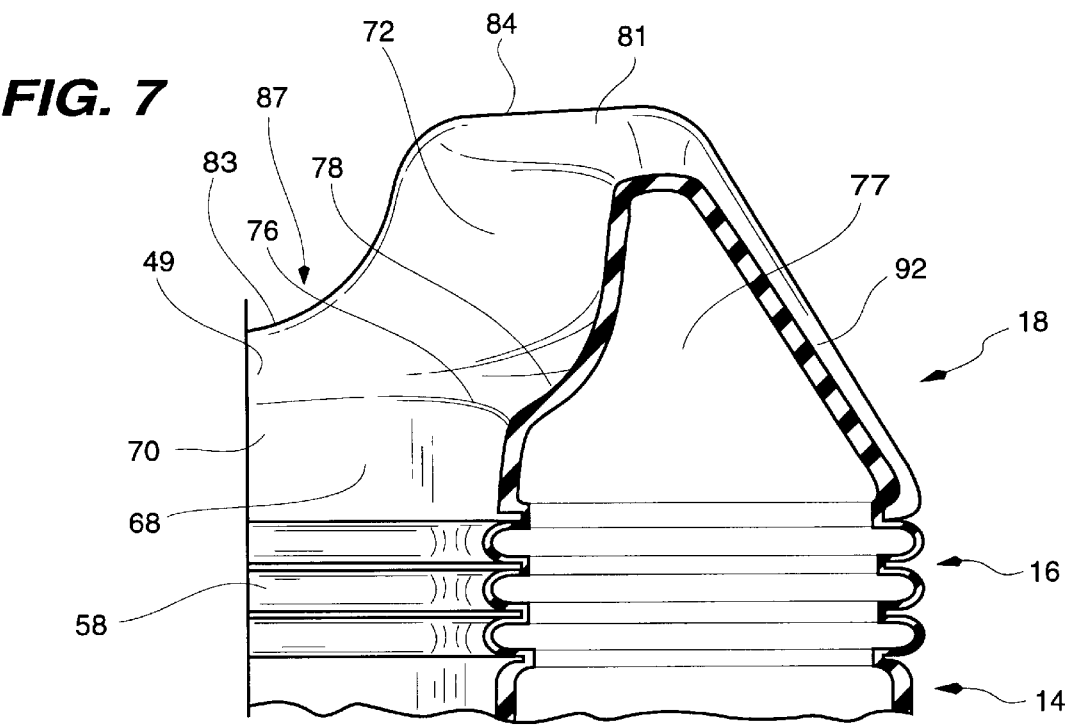

INFLATABLE CERVICAL TRACTION OR STRETCH DEVICE

CROSS REFERENCE TO RELATED APPLICATIONS

This application is a continuation-in-part of U.S. application Ser. No. 08/516,007, filed Aug. 16, 1995, a continuation-in-part of U.S. application, Ser. No. 08/327,021 filed on Oct. 21, 1994, now U.S. Pat. No. 5,569,175 issued Oct. 29, 1996, a continuation-in-part of U.S. application Ser. No. 08/303,691 filed Sep. 9, 1994, now U.S. Pat. No. 5,454,781, issued Oct. 3, 1995, and a continuation-in-part of U.S. application Ser. No. 08/120,602 filed on Sep. 13, 1993, now U.S. Pat. No. 5,441,479, issued Aug. 15, 1995.

BACKGROUND OF THE INVENTION

1. Field of the Invention.

The present invention relates to an inflatable, one-piece cervical traction/stretch device which is positioned around or under the neck of a user who can be lying on a flat surface and between the shoulders and the head of the user and which includes an expandable, inflatable body made of a elastically expandable material and which can have a shoulder portion, a bellows portion and a head portion. A hand operated bulb type air pump with a manually operated air pressure relief valve is connected to the bellows portion for manually expanding and contracting the bellows portion thereby to stretch the neck and release stretching force on the neck.

2. Description of the Related art Including Information Disclosed Under 37 CFR §§ 1.97–1.99.

Heretofore it has been proposed to provide a traction pillow and a inflatable cervical traction pillow.

Examples of such pillows are disclosed in the following two U.S. Patents:

| U.S. Pat. No. | Patentee |
|---|---|
| 5,060,661 | Howard |
| 4,832,007 | Davis, Jr. et al. |
| 4,805,603 | Cumberland |
| 4,771,493 | Park |
| 4,732,144 | Cunanan |

In the Howard U.S. Pat. No. 5,060,661 there is disclosed an inflatable neck and head support for use by a wearer which include a generally rectangular body of flexible gas impervious material with two side panels that are sealed around the entire periphery of the support to form a closed chamber. Fastening structure are mounted on spaced apart portions of the body to permit securing of the rectangular shaped body into an annular shape to encompass the neck and support the head of a wearer.

In the U.S. Pat. No. 4,832,007 to Davis, Jr. et al. there is disclosed a traction pillow and method for using same. The pillow is made of resilient material and has a generally rotatable portion (cervical roll) for supporting the cervical region of a user. The cervical pillow has cavities therein which enable a medical technician to collapse the pillow by pressing down on it while the patient's neck is resting on the pillow.

In the Cumberland U.S. Pat. No. 4,805,603 there is disclosed a cervical traction apparatus comprising a head/neck/shoulder support unit having a vertical slot in the region corresponding to the cervical area. The slot separates the unit into a first section and a second section. The upper surfaces of each of the sections is shaped to receive the head, neck and shoulders of a reclining person. An inflatable air sack is located within the unit between the first and second sections and a hand operated bulb type air pump is provided for pumping up the air sack.

The Park U.S. Pat. No. 4,771,493 discloses an adjustable therapeutic pillow for applying a gentle traction force to the head, neck and shoulders region of a user. The apparatus includes a base, first and second pillow members having spaced apart convex pillow surfaces for engagement with the user, and structure for fastening the pillow members to a base. The apparatus is adjustable in that both the lateral spacing of the pillow members and the overall length of the pillow members may be adjusted.

The Park U.S. Pat. No. 4,732,144 discloses a multi-section emergency neck immobilizing brace which incorporates a frame structure, which is adapted for mounting on the shoulders of a patient and which is securable to the patient's body by straps. A brace frame mounts a head halter with a two-point strap suspension and with a ratchet mechanism which can be pivoted out of or into an operative position for placing the patient's head in traction. Inflatable cushion devices limit forward, backward and lateral movement of the patient's head after the head is placed in traction and provide an air cushioned restraint.

SUMMARY OF THE INVENTION

According to the present invention there is provided a cervical traction or stretch device comprising: an inflatable and expandable bladder or bellows having an undulating or pleated wall and a central U-shaped space so that the bladder or bellows can extend at least part way around the neck of a user with the undulating or pleated wall extending transversely of the user's neck. A pumping mechanism is provided coupled to the bladder or bellows and operable by a user for pumping air into the bladder or bellows for expanding same. The bladder or bellows has an upper side and a lower side with the lower side being constructed and arranged to be positioned adjacent a user's shoulders and exert pressure thereagainst when the bladder or bellows is inflated and expanded and the upper side being constructed and arranged to engage and exert pressure against the base of a user's head when the bladder or bellows is inflated and expanded.

BRIEF DESCRIPTION OF THE DRAWINGS

FIG. 2 is a top plan view of a body of the inflatable cervical traction/stretch device shown in FIG. 1.

FIG. 3 is an end plan view of the body of the cervical traction/stretch device shown in FIG. 2 and is taken along line 3—3 of FIG. 2.

FIG. 6 is a sectional view through the body of the cervical traction/stretch device shown in FIG. 2 and is taken along line 6—6 of FIG. 2.

FIG. 7 is a sectional view through a head portion of the body of the cervical traction/stretch device and is taken along line 7—7 of FIG. 3.

DESCRIPTION OF THE PREFERRED EMBODIMENT

Figure 1:
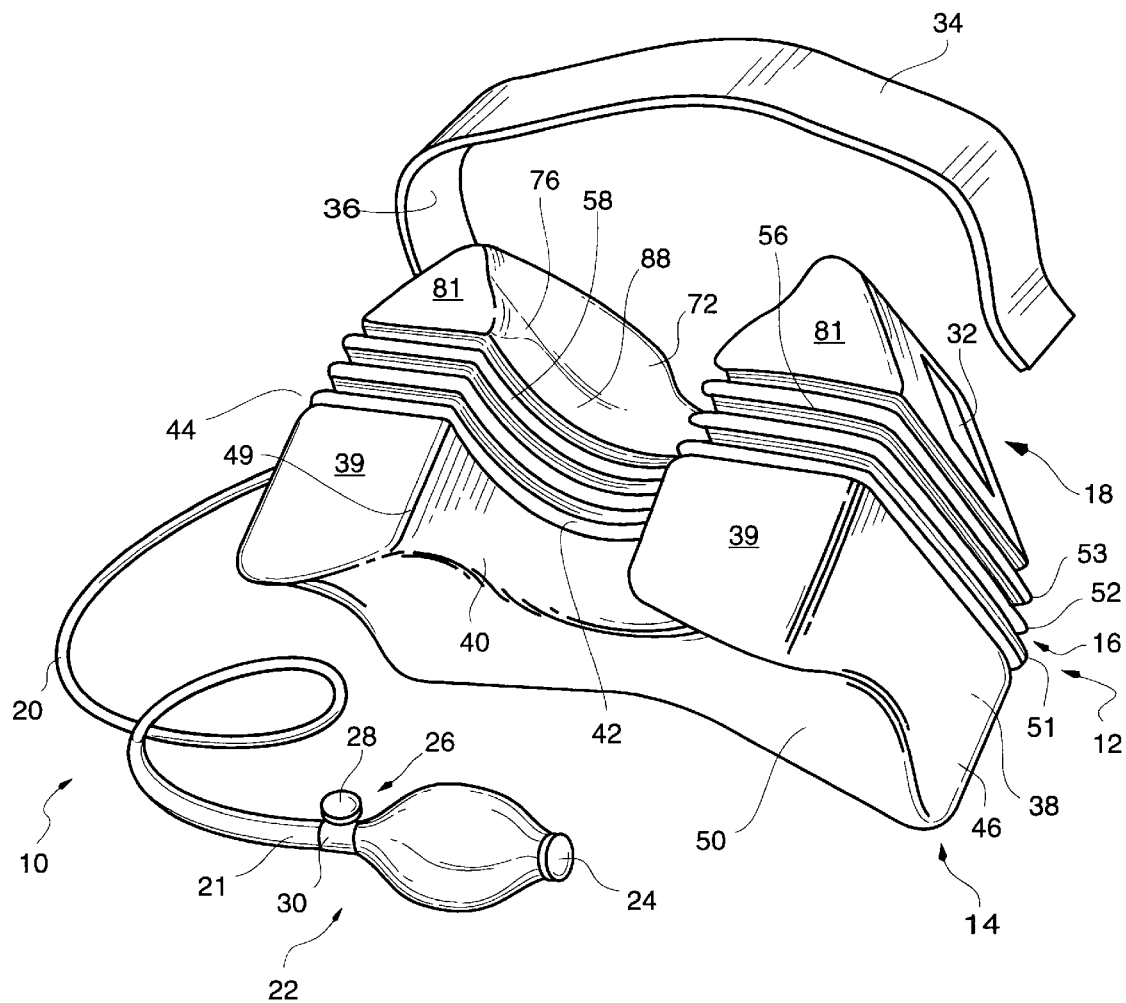
FIG. 1 is a perspective view of the inflatable cervical traction/stretch device constructed according to the teachings of the present invention.

Referring now to the drawings in greater detail there is illustrated in FIG. 1 an inflatable cervical traction/stretch device 10 constructed according to the teachings of the present invention. The device 10 includes a body 12 including a shoulder portion 14, a bladder or bellows portion 16, and a head portion 18.

As shown in FIG. 1, the device is inflated in a first inflated condition from an un-inflated condition (not shown) in which the shoulder portion 14, the bellows portion 16 and the head portion 18 are completely deflated.

The shoulder portion 14, the bladder or bellows portion 16 and the head portion 18 are made of an elastically expandable material, such as rubber, and when in the first inflated condition, have sufficient rigidity or hardness to establish traction, stretching or lift surfaces thereby to enable maximum traction forces to be created.

The cervical traction or stretch device 10 further includes a tubing 20 connected to the bellows portion 16 and having, at an outer end 21 thereof, an air pump 22 in the form of compressible bulb 22 for pumping the cervical traction or stretch device 10 with air. The compressible bulb 22 has, at its outer end, a one way inlet valve 24 which allows air to be sucked into the bulb 22, but does not allow air to flow out of the bulb 22 when it is compressed.

Adjacent to the bulb 22 and mounted on the tubing 20 is a relief valve 26 which comprises a knurled thumbscrew 28 mounted in a metal collar 30 fixed to the tubing 20. When the thumbscrew 28 is rotated into the collar 30, no air can escape from the cervical traction or stretch device 10 and when the thumbscrew 28 is threaded outwardly, the valve 26 is opened to allow compressed air to escape from the cervical traction or stretch device 10 through the tubing 20 and out of the relief valve 26.

Figure 8:
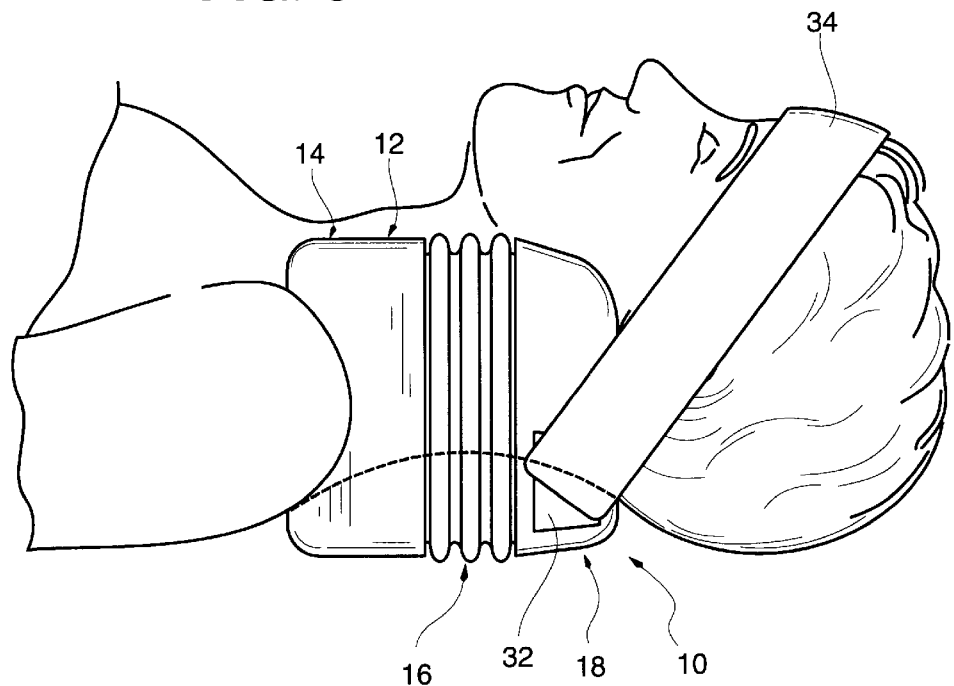
FIG. 8 is a side plan view of the cervical traction/stretch device with the neck of a patient resting therein and with the device being in a inflated but non-extended condition.
Figure 9:
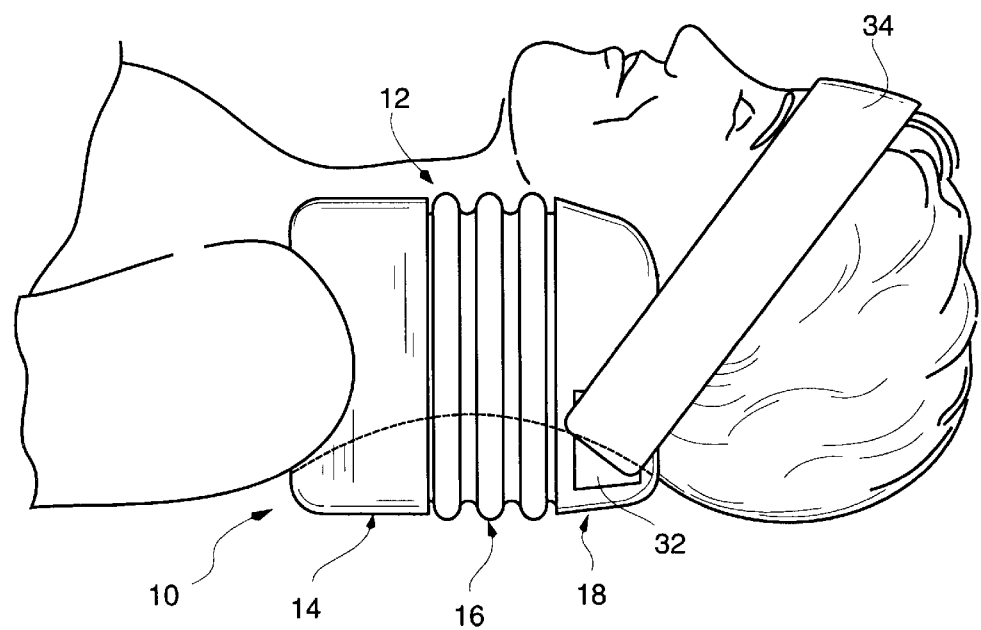
FIG. 9 is a side elevational view of a patient resting in the cervical traction/stretch device, similar to the view shown in FIG. 8, but showing the cervical traction/stretch device in an inflated and extended condition for stretching or placing traction on the patient's neck.

In addition to the compressible bulb 22 and the tubing 20, the cervical traction or stretch device 10 includes, on either side of the head portion 18, loop and hook type fastening structure 31, 32 (FIG. 3) of the type sold under the trademark VELCRO ® and a head strap 34 which is adapted to be received over a patient's head. The strap 34 has on its inner surface 36 a fabric texture which is adapted to attach to the fastening structures 31 and 32. This is shown in FIGS. 8 and 9 where there is shown a patient's head resting in the cervical traction or stretch device 10 with the shoulder portion 14 bearing against the patient's shoulders and the patient's head being received in the head portion 18 with the head strap 34 extending over the forehead and being connected to the fastening structures 31 and 32 on either side of the head portion 18.

When inflated to a first condition, as shown in FIGS. 2–7, the shoulder portion 14 is contoured to rest on the shoulders of a patient for enabling a counter-stretch force to be created by the cervical traction or stretch device 10. In this respect, it will be noted that the shoulder portion 14, the bellows portion 16 and the hand portion 18 have various specially shaped curved surfaces for allowing the device 10 to create comfortable and therapeutic stretching to a patient's neck. These specially shaped curved surfaces are described below briefly and are described in detail in the parent U.S. Pat. No. 5,441,479 of which this application is a continuation-in-part.

The shoulder portion 14 has a bottom 36, opposite end walls 37 and 38, a contoured curved outer end surface 40 and an arcuate, semi-cylindrical or U-shaped surface 42 that extends downwardly from the top side 39 in the middle area thereof between two spaced apart block portions 44 and 46 of the shoulder portion 14.

As best shown in FIG. 1, the outer end surface 40 of the shoulder portion 14 inclines slightly inwardly towards the bellows portion 16 from each side wall 37 and 38 of the shoulder portion 14 to the middle of the shoulder portion 14 to accommodate the natural sloping of a patient's shoulders. Also from top to bottom, the contoured end surface 40 is curved inwardly and then outwardly to form arcuate surfaces 49 or 50 on the respective block portions 44 and 46 which are received over the natural contour of a patient's left and right shoulders. The extent of the U-shaped surface 42 varies from approximately 1" in the middle area of the body 12 to approximately 2" at the top side 39.

The construction of the curved outer end surface 40 of the shoulder portion 14 enables the shoulder portion 14 to fit easily over the front and center portions of the shoulders of a patient or user to enable a better and more manageable stretch force to be applied against the patient's shoulders with a minimum of slippage.

The bellows portion 16 is constructed with a plurality, e.g., three undulations 51, 52 and 53 in the illustrated embodiment and is constructed and arranged to raise and support the cervical curve of a patient's neck during inflation. Also, to provide an even force along the width of the shoulder portion 14 and most importantly, along the width of the head portion 18.

The bellows portion 16 is generally rectangular and extends substantially the full height and width of the body 12 of the device 10. The bellows portion 16 has a top side 56 and an arcuate, semi-circular or U-shaped surface 58 extending downwardly from the top side 56 generally aligned with the U-shaped surface 42 of the shoulder portion 14 to provide a nesting support for a patient's neck.

Most cervical injuries to patients involve the loss of the natural cervical curve forming a so called military neck or straight neck syndrome. This creates stress on the upper thoracic muscles, as these muscles are forced to hold the head upright. When the natural curve is in place, the head weight is distributed throughout the skeletal system. The body 12 of the cervical traction or stretch device 10 is constructed so that the patient's cervical curve is supported to relieve upper thoracic muscles from unnatural stress. The manner in which the shoulder portion 14 achieves this function at the center of the body 12 of the cervical traction or stretch device 10 is shown in FIG. 4 where the contoured surface 40 has a downwardly inclined portion 60 going up to a flat or slightly upwardly inclined surface portion 62 of the U-shaped surface 42.

Like the shoulder portion 14, the head portion 18 is also integrally formed with the bellows portion 16. The head portion 18 has a generally arcuate or semi-cylindrical U-shaped surface 68 having a portion 70 (see FIG. 3) that inclines slightly downwardly at the center to fit the cervical curve of the patient's neck and has a head receiving surface 72 having a center portion 74 that curves downwardly for mating with the cervical curve.

The U-shaped surface 68 extends toward the outer end of the head portion 18 a distance approximately ¾ of an inch to one inch and forms a shoulder 76 on opposite sides of the U-shaped curved surface 68 but not at the center of the U-shaped curved surface 68. This can be best seen in FIGS. 4, 5 and 6.

Figure 4:
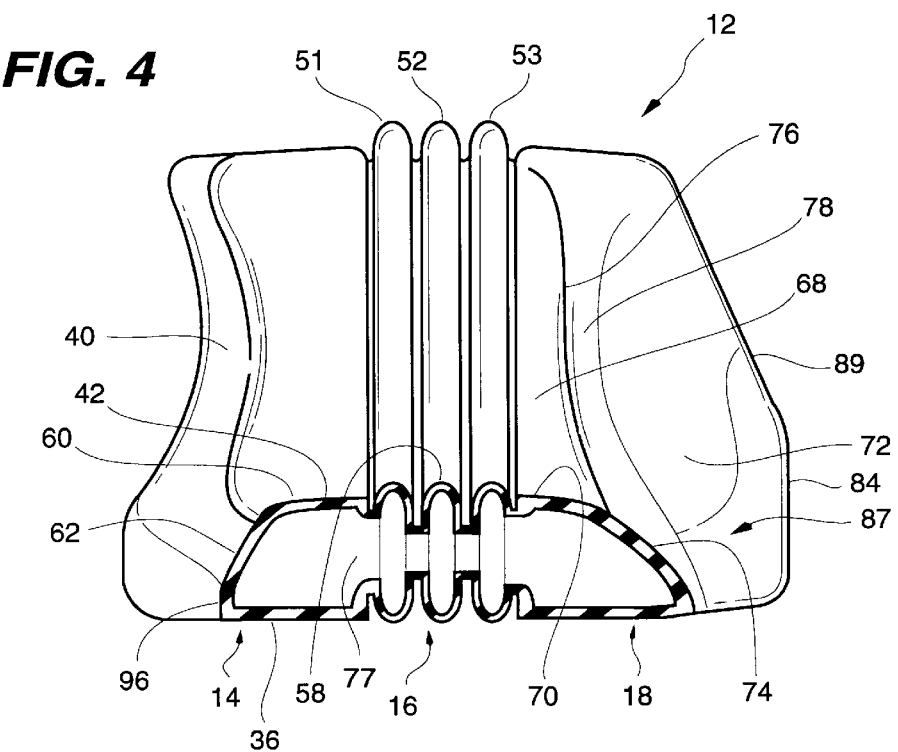
FIG. 4 is a sectional view through the body of the cervical traction/stretch device shown in FIG. 2 and is taken along line 4—4 of FIG. 2.

As shown in FIG. 4, there is very little of the shoulder 76, with the U-shaped surface 68, 70, at the bottom of the U connecting with the surface portion 74 of the head receiving surface 72.

Figure 5:
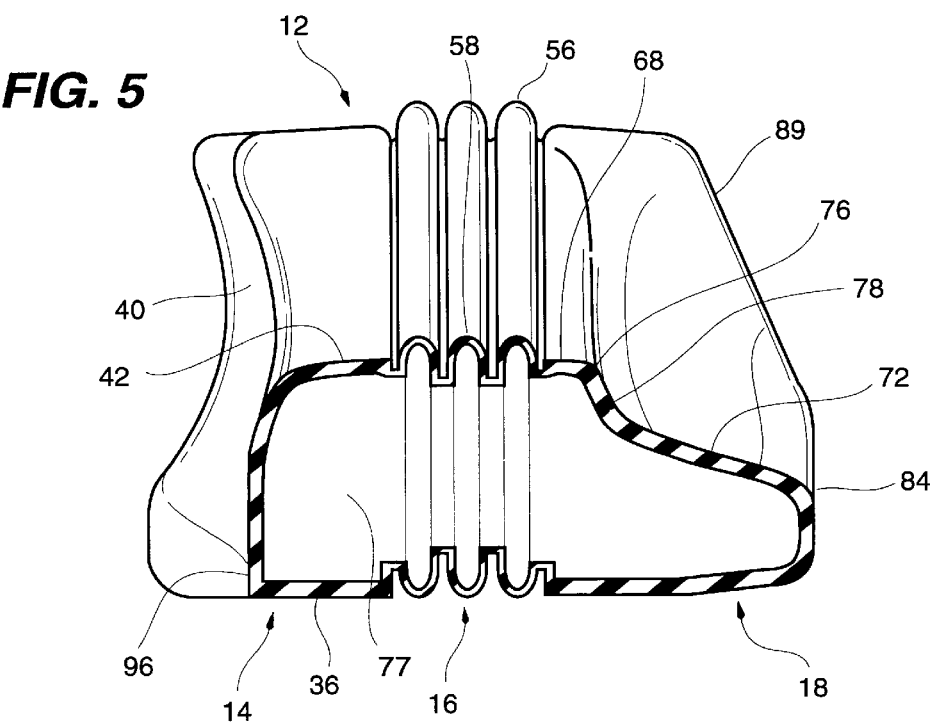
FIG. 5 is a sectional view through the body of the cervical traction/stretch device shown in FIG. 2 and is taken along line 5—5 of FIG. 2.

Also, as shown in FIGS. 4, 5 and 6, the inside of the inflatable cervical traction or stretch device 10 is a hollow chamber 77 which encompasses the combined interior of the shoulder portion 14, the bellows portion 16 and the head portion 18.

The thickness of the rubber material that forms the device 10 is generally uniform throughout the horizontal and vertical cross section of the shoulder portion 14 as shown in FIGS. 4, 5, 6 and 7. Also, the thickness of the material throughout the horizontal and vertical cross section of the head portion 18 is uniform. Finally, the thickness of the material throughout the horizontal and vertical cross section of the bellows portion 16 is also uniform. However, preferably, the rubber material is thicker in the shoulder portion 14 and the head portion 18 than in the bellows portion 16.

The thicker material in the shoulder portion 14 and the head portion 18 results in the bellows portion 16 being more readily expandable than the shoulder portion 14 and the head portion 18. Consequently, once the device 20 is inflated from the un-inflated condition to the first inflated condition to take the shape shown in FIGS. 2–7, further inflation of the device causes the bellows portion 16 to expand a greater amount than the head and shoulder portions 14 and 18. The shoulder portion 14 and the head portion 16 remain inflated in a shape similar to the first inflated condition and do not become distorted while further expanding.

The further expansion of the bellows portion 16 occurs through the expansion of the undulations in the bellows portion 16, e.g. undulations 51, 52 and 53, in a controlled manner, to cause even pressure against and separation of the shoulder portion 14 and the head portion 18. This expansion causes comfortable and therapeutic stretching to a patient's neck, while allowing the shoulder portion 14 and the head portion 18 to maintain the traction, stretching or lift surfaces created when the device 10 is inflated to the first condition.

As shown in FIG. 5, part way up either side of the U-shaped surface 68 the shoulder 76 is pronounced and is located at the junction between the U-shaped surface 68 and the specially contoured head receiving surface 72. The shoulder 76 at this location is adapted to bear against the occipital bone and defines in the head receiving surface an occipital cervical pressure or lift surface 78 just outwardly of the shoulder 76.

This shoulder 76 and the adjacent pressure or lift surface 78 on the head receiving surface 72 enables the head portion 18 to apply pressure at the region of the occipital bone of a patient on each side of the neck. It is believed that this pressure on the occipital bone applied with the cervical traction or stretch device 10 of the present invention also can alleviate or relieve headache pain.

Looking now at FIGS. 4, 5 and 6 it will be appreciated that the body 12 has in the U-shaped openings and at the center of the U-shaped surfaces 42, 58, 68 the curved straight or inclined surface portions 62, 60, 42, 58, 70, and 74 for receiving the cervical curve of the neck (FIG. 4). Then as one moves to the left side or the right side of the U-shaped openings in the area of the U-shaped opening in the head portion 18, the head receiving surface 72 has the pronounced shoulder 76, the occipital bone receiving surface 78 and then a gentle sloping curving surface portion 80 (FIG. 6) for supporting the head above the occipital bone on each side of the head.

As shown in FIG. 6, near a top side 81 of the head portion 18, the U-shaped surface 68 slopes in a longitudinal direction downwardly and merges in or with a smooth downwardly extending curved surface portion 82 of the head receiving surface 72 which extends to an outer end 84 of the head portion 18 on each side of the head receiving surface 72.

The U-shaped opening 58 in the bellows portion 16 has, in the extended or inflated condition, a depth of between 3 and 4 inches and preferably 3 and ½ inches.

Looking now at FIG. 2, it will be apparent that the specially contoured head receiving surface 72 extends downwardly to a bottom 86 (FIG. 3) in the central area of the head portion 18 such that the head portion has a U-shaped notch 87 at the bottom thereof where the head of a patient can then rest on a flat surface.

Then the ends 84 of the head portion 18, on either side of the center thereof, has left and right end wall portions 87, 88 extending upwardly from the flat bottom 86 of the head portion 18 to sloping end wall portions 89, 90 which slope upwardly and inwardly toward the top side 81 of the head portion 18.

Also, as best shown in FIG. 2 left and right outer sides 91, 92 of the head portion 18 are inclined from the bellows portion 16 inwardly and outwardly to the upwardly and inwardly inclined end wall portions 89, 90. On each of these left and right outer sides 91, 92 there is provided the patches 31, 32 (FIG. 3) of hook and loop attaching material of the type sold under the trademark VELCRO®. Each patch 31, 32 is located on the inclined side 91 or 92 adjacent the bottom 86.

If desired, the bottom 86 of the head portion 18 can have an inclined slot or flute 94 or 95 therein on either side of the U-shaped notch 87 as shown in FIG. 3.

As best shown in FIGS. 1, 8 and 9 the head strap 34 has a fabric attachment structure 36 of the type sold under the trademark VELCRO® on the inside 36 of the strap 34 which, at each end of the strap 34, is adapted to be received over a patient's forehead and secured to the patches 31, 32 to securely hold the patient's head to the head portion 18 of the body 12 of the cervical traction or stretch device 10 to achieve the greatest stretch or traction.

In the use of the cervical traction or stretch device 10 a user or patient will inflate the device from the un-inflated condition to the first inflated condition. Then the person will rotate the thumbscrew 28 to prevent air from escaping from the device 10. Then the person will place the inflated device 10 on a flat surface such as a floor or table and lay down on the floor or table with the cervical curve of the patient's neck received over the center of the U-shaped opening formed by the U-shaped opening, i.e., over surfaces or surface portions 62, 60, 42, 58, 72, 74, in the shoulder portion 14, the bellows portion 16 and the head portion 18. Then the user or patient or a doctor or other medical technician will place the strap 34 over the head of the user or patient and secure it firmly to the patches 31, 32. Next, the user, or a medical technician will pump the hand-held bulb type air pump 22 to further inflate the device 10 to the second inflated condition where the bellows portion 16 is expanded to create traction on the cervical area of the patient's neck supported by the surface portions 62, 60, 42, 58, 72, 74, in the shoulder portion 14, the bellows portion 16 and the head portion 18.

If desired an electrically operated air pump (not shown) can be connected to the tubing 20 in place of the bulb type hand-operated air pump 22. Such an electronic pump will include a timer for cycling the electrical pump through intermittent pump and relief cycles thereby to apply intermittent traction or stretch to the patient's neck for treating soft tissue or disk dysfunctions, not limited to arthritis, of a patent. Intermittent traction or stretch is preferred by healthcare professionals as a method of treatment. In this modification, air can be pumped into or released out of the bellows portion 54 under the control of a timer having several different time cycles.

A user, patient or clinician can achieve some of the same benefits of electrically controlled intermittent traction or stretch by intermittently pumping the inflation bulb 22 and operating the release valve 26.

From the foregoing description, it will be apparent that the cervical traction or stretch device 10 of the present invention has a number of advantages, some of which have been described above and others of which are inherent in the invention.

Also from the foregoing description it will be apparent that modifications can be made to the cervical traction or stretch device 10 without departing from the teachings of the invention.

Accordingly the scope of the invention is only to be limited as necessitated by the accompanying claims.

I claim:

1. A cervical traction or stretch device comprising: an inflatable and expandable bladder or bellows having an undulating or pleated wall and a central U-shaped space so that said bladder or bellows can extend at least part way around the neck of a user with said undulating or pleated wall extending transversely of the user's neck; and a pumping mechanism coupled to said bladder or bellows and operable by a user for pumping air into said bladder or bellows for expanding same; said bladder or bellows having an upper side and a lower side; said lower side being constructed and arranged to be positioned adjacent a user's shoulders and exert pressure thereagainst when said bladder or bellows is inflated and expanded; and said upper side being constructed and arranged to engage and exert pressure against the base of a user's head when said bladder or bellows is inflated and expanded.

2. The cervical traction or stretch device of claim 1 wherein said pumping means for pumping air into said bladder or bellows includes a conduit and a bulb type air pump at the outer end of said conduit; said bulb type air pump having a one way inlet valve at an outer end thereof and, at an inner end thereof, a manually operated relief valve.

3. The cervical traction or stretch device of claim 1 wherein said means for pumping air into said bladder or bellows includes means for intermittently pumping air into and releasing air out of said bladder or bellows for treating soft tissue or disk dysfunctions, including arthritis, in the neck of a user.

4. The cervical traction or stretch device of claim 3 wherein said means for pumping air into said bladder or bellows includes an electrically operated pump and a timer for controlling operation of said electrically operated pump whereby air can be intermittently pumped into and out of said bladder or bellows for treating soft tissue or disk dysfunctions, including arthritis, in the neck of a user.

* * * * *